United States Patent

Horino et al.

Patent Number: 5,458,976
Date of Patent: Oct. 17, 1995

[54] WATER AND OIL REPELLANT COATED POWDERS AND METHOD FOR PRODUCING SAME

[75] Inventors: Masaakira Horino; Nami Ito, both of Yokohama, Japan

[73] Assignee: Matsushita Electric Industrial Co., Ltd., Osaka, Japan

[21] Appl. No.: 264,237

[22] Filed: Jun. 22, 1994

Related U.S. Application Data

[63] Continuation of Ser. No. 983,296, Nov. 30, 1992, abandoned, which is a continuation of Ser. No. 359,776, May 31, 1989, abandoned.

[30] Foreign Application Priority Data

Jun. 17, 1988 [JP] Japan ................................. 63-148345
Nov. 7, 1988 [JP] Japan ................................. 63-279334

[51] Int. Cl.$^6$ ........................................... A61K 9/14
[52] U.S. Cl. .................... 428/405; 106/2; 424/63; 424/69; 424/401
[58] Field of Search ..................... 428/403, 404, 428/405; 424/63, 69, 401; 106/2

[56] References Cited

U.S. PATENT DOCUMENTS

| | | | |
|---|---|---|---|
| 3,632,744 | 1/1972 | Paulsen . | |
| 3,997,507 | 12/1976 | Kirimoto et al. | 428/264 |
| 4,032,495 | 6/1977 | Perronin et al. | 428/421 |
| 4,111,700 | 9/1978 | Connick, Jr. et al. | 106/2 |
| 4,417,024 | 11/1983 | Koda et al. | 524/861 |
| 4,525,425 | 6/1985 | Church | 428/428 |
| 4,640,943 | 2/1987 | Meguro et al. | 523/200 |
| 4,642,356 | 2/1987 | Langner et al. | 549/214 |
| 4,801,445 | 1/1989 | Fukui et al. | 428/407 |
| 4,833,188 | 5/1989 | Kortmann et al. | 524/217 |
| 4,863,762 | 9/1989 | Aramaki et al. | 427/255.6 |
| 4,863,800 | 9/1989 | Miyoshi et al. | 428/403 |
| 4,919,922 | 4/1990 | Miyoshi et al. | 428/407 |

FOREIGN PATENT DOCUMENTS

| | | |
|---|---|---|
| 0168645 | 1/1986 | European Pat. Off. . |
| 55-136213 | 10/1980 | Japan . |
| 55-167209 | 12/1980 | Japan ................. 424/63 |
| 1199055 | 7/1970 | United Kingdom ........ 106/2 |

*Primary Examiner*—Jenna L. Davis

[57] ABSTRACT

A water and oil repellant vapor deposition coating layer is produced by reaction-bonding a water and oil repellant agent to an active site, either an acid or base site, on the surface of an inorganic base powder. The water and oil repellant agent is a fluorosilane, fluorosilazane or fluorinated hydrocarbon. The water and oil repellant coated powder is produced by coating the activated inorganic powder with either a water and oil repellant agent or an oily agent, or both, a reactive auxiliary agent and a primer. The first baked coating layer is formed on the surface of the base powder by heat treatment and a second baked coating layer may be formed on the first baked coating layer by heat treatment, in which the second baked coating layer is formed with the reactive auxiliary agent and either the water and oil repellant agent or the oily agent, or both, to provide a multi-layer structure on the powder. The baked coating layer is reaction-bonded to an activated inorganic base powder and has a cross-linked network structure.

20 Claims, 1 Drawing Sheet

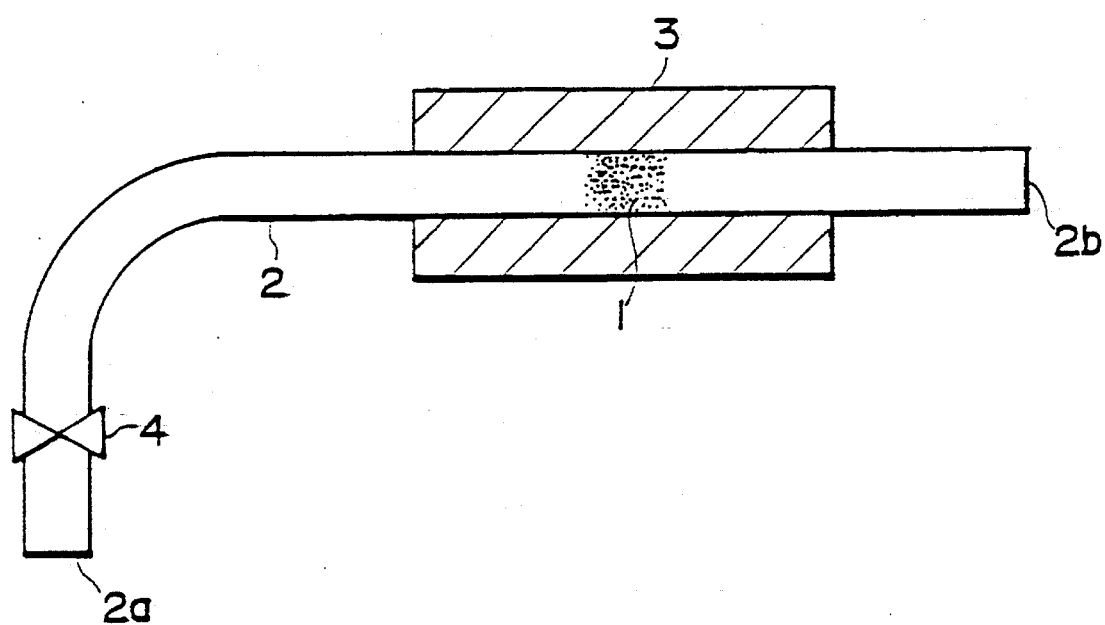

WATER AND OIL REPELLANT COATED POWDERS AND METHOD FOR PRODUCING SAME

This application is a continuation of U.S. application Ser. No. 07/983,296, filed Nov. 30, 1992 which is a continuation of U.S. application Ser. No. 07/359,776, filed May 31, 1989, both now abandoned.

FIELD OF THE INVENTION

This invention relates to a water and oil repellant coated powders, above all, those intended for make-up cosmetics, and the method for producing the same. This invention also relates to the method for producing water and oil repellant coated powders that may be used for preparation of make-up cosmetics which do not suffer from unevenness or makeup dry of makeup finish due to water, perspiration or sebum, and which can provide smooth spread to form an even applied cosmetic thin layer due to suppressed flocculation of the powder particles.

BACKGROUND OF THE INVENTION

The powders, such as pigments, used in the make-up cosmetics currently generally supplied to the market, especially those of the loose or solid type, are usually complex oxides and are endowed with hydroxy groups on their surface, with the amount of the hydroxy groups differing depending on the types of the powders. In titanium oxide powders, as a typical example of these powders, there exists a minor amount of weakly reactive hydroxy groups or adsorbed water as demonstrated by the analysis of the moisture produced on heating, with the moisture content of the water-containing titanium oxide ranging between 15 to 30 wt %. The powders, such as pigment powders, differ in their degree of surface hydrophilicity or lipophilicity according to the types of the powders, while there co-exist various powders having different degrees of surface activity. In addition, the reason why the makeup finish tends to be transparent or uneven or to exhibit insufficient tight-adhering feel may be thought to reside in (a) change in the particle size or deformation in particle shape due to mechanical impact on the minute surfaces, difference in wetting by secretions such as water, perspiration or sebum due in turn to the difference in surface activity caused by freshly produced surfaces; and (b) the difference in the amount of the oily agent physically affixed or adsorbed with a non-uniform weak force on the powder surface or in the HLB of the oily agent, or the segregation of the oil contents due to mechanical impact in the course of the preparation. That is, conventional cosmetics are subjected to flocculation or changes in the refractive index of the cosmetic powders on account of changes in wetting of the powders by water, perspiration or sebum, and hence to unevenness or makeup dry of makeup finish, which are counted for disadvantages in the art.

The following methods and cosmetics are known in the art as means to overcome these deficiencies:
i) The method of surface treatment of the powders with surfactants;
ii) the method of surface treatment of lecitin or N-stearoyl-aluminum L glutaminate;
iii) the method of heat-treating the powder surface with methyl hydropolysiloxane;
iv) the method of processing the powder surface with alcoholic compounds; and
v) "Cosmetics mainly consisting of cosmetic powders and a coloring agent characterized in that the cosmetics are admixed with cosmetic powders and/or coloring agent treated with a water and oil repellant agent consisting of a fluorine containing polymer" according to the JP Patent Kokoku Publication (JP-Kokoku) Go. 61-55481/1986, and "Cosmetics mainly consisting of cosmetic powders and/or a coloring agent characterized in that the cosmetics are admixed with cosmetic powders and/or a coloring agent surface-treated with a fluorine-containing resin, according to JP Patent Kokoku No. 61-48803/1986.

The above cited conventional technology has however the following disadvantages.
(i) The method of surface treatment of the powder with metal soap-surfactant.

The cosmetics treated with metal soap such as aluminum stearate, zinc stearate or zinc myristate is water-repellant, but is not oil-repellant. Thus the cosmetics are not resistant to sebum and become uneven due to exuded sebum. The cosmetics also become no longer water-repellant depending on selection of surfactants. The cosmetics are similar to metal soap as long as the resistance to sebum or fat is concerned.

These agents are simply affixed or adsorbed physically to the powder surface and hence may be affixed or adsorbed unevenly or inferior in water repellancy depending on the production method employed.
(ii) The method of surface-treating the powder surface with lecitin or stearoyl-aluminum L-glutaminate.

The cosmetics exhibit affinity to skin and some water and oil repellancy but only to a lesser extent. More over, since surface treatment agents, such as lecitin, are adhered physically to the powders, the surface treatment agents tend to become desorbed from the powders under the strong shearing force caused by the mechanical force in the course of the production process of the cosmetics, while the makeup finish tends to become transparent by water or perspiration or be subjected to shine of makeup finish due to sebum.
(iii) The method of heat-treating the powder surface with methyl hydropolysiloxane.

Silicon oils exemplified by methyl hydropolysiloxane are satisfactory in water repellancy, but are rather inferior in oil repellancy. The commercial cosmetics, produced by reacting the silicon oil with hydroxy groups on the powder surface, are somewhat inferior in water repellancy and practically nil in oil repellancy. It is because a number of hydroxy groups and hydroxy groups of methyl hydropolysiloxane remain unreacted and only a few of these hydroxy groups take part in chemical bonding.
(iv) The method of treating the powder surface with alcoholic compounds.

The method is effective to protect the hydroxy groups on the powder surface. Although the produced cosmetics are improved as to the tendency to become transparent due to wetting, they are only low in adhesion to skin and the makeup finish tends to become uneven.
(v) The surface-treated cosmetic powders in the cosmetics produced in the JP Kokoku Nos. 61-55481/1986 and 61-48803/1986 are inferior in water and oil repellancy, with only a few group of the powders and the surface treatment agent taking part in the reaction. The cosmetics containing pigments free of hydroxy groups, such as titanium oxide, are entirely unsatisfactory as to the water and oil repellancy since the groups taking part in chemical bonding are substantially nil.

SUMMARY OF THE DISCLOSURE

It is a principal object of the present invention to overcome the above described drawbacks in the prior art technology and to provide water and oil repellant coated powders which may be used to produce cosmetics free from uneveness or makeup dry of the makeup finish due to water, perspiration or sebum, and which can provide smooth spread to form an even applied cosmetic thin layer, and a method for producing the coated powders.

According to an aspect of the present invention, the above object may be accomplished by:

(1-1) a water and oil repellant coated powder having a vapor deposition coating layer of the water and oil repellant agent on the surface of an inorganic base powder, said coating layer being chemically bonded to an active site on the surface of the inorganic base powder; and (1-2) A method for producing a water and oil repellant coated powders comprising contact-reacting an inorganic base powder with a gaseous water and oil repellant agent under heating to form the vapor deposition coating layer of the water and oil repellant agent on the surface of said base powder, said coating layer being bonded to the active site on the surface of said base powder.

The coating layer of the coated powders according to the present invention (First aspect) is not only both water and oil repellant, but is tough and strongly bonded with the inorganic base powder surface, so that the water and oil repellancy of the powders is not impaired. Hence the cosmetics containing the coated powders of the present invention remain free from the tendency to become transparent due to water, perspiration or sebum or from uneveness or makeup dry of the makeup finish for a prolonged time.

Also, the method of the present invention (First aspect) is a simplified and industrially advantageous production method in which curing is not required and the coated powders may be produced in a shorter time. When the clay minerals are used as the inorganic powder powder base, the coated powders may be produced without the crystal structure disappearing or becoming amorphous and the cosmetics containing these coated powders exhibit satisfactory feeling due to the presence of the clay minerals.

According to the second aspect of the present invention, the above object may be accomplished by the following methods for producing the coated powders:

(2-1) The method for producing a coated powder comprising:

coating an activated inorganic base powder with one or both of a water and oil repellant agent and an oily agent, a reactive auxiliary agent and a primer, and forming a baked coating layer on the surface of said base powder by heat treatment, said baked coating layer being formed of one or both of the water and oil repellant agent and the oily agent and said reactive auxiliary agent.

(2-2) The method for producing a coated powder comprising:

providing an activated inorganic base powder on its surface having a first baked coating layer of one or both of a water and oil repellant agent and an oily agent and a reactive auxiliary agent, and forming a second baked coating layer on the surface of a first baked coating layer by heat treatment, said second baked coating layer being formed of one or both of the water and oil repellant agent and the oily agent and said reactive auxiliary agent, to provide a multilayer structure, said first layer being formed of one or both of the water and oil repellant agent and the oily agent and the reactive auxiliary agent, provided that said second layer contains the water and oil repellant agent when said first layer is devoid of the water and oil repellant agent.

(2-3) The method for producing a coated powder comprising:

providing an activated inorganic base powder on its surface having a first baked coating layer of one or both of a water and oil repellant agent and an oily agent, a reactive auxiliary agent and a primer, and forming a second baked coating layer on the surface of a first baked coating layer by heat treatment, said second baked coating layer being formed of one or both of the water and oil repellant agent and the oily agent to provide a multilayered structure.

According to the present invention (Second aspect), the water and oil repellant agent, reactive auxiliary agent and oily agent may be reaction-bonded on the inorganic base powder surface in a completed or nearly completed form. On the other hand, the water and oil repellant agent, reactive auxiliary agent and the oily agent may be bonded to the usually-difficultly-reactable inorganic base powder surface, while it becomes possible to promote the reaction between the same or different water and oil repellant agent(s), reactive auxiliary agent(s) and oily agent(s).

Thus the coated powder s produced by the present invention (Second aspect) are excellent in water and oil repellancy and are not destroyed easily since the dense and compact coating layer is strongly bonded by heat treatment to the inorganic base powder. The cosmetics containing the coated powders remain free from the tendency to become transparent or from uneveness or make-up dry of makeup finish due to water, perspiration or sebum for a prolonged time.

When the activated inorganic base powder is produced by grinding (abrasive milling), the production process may be shortened without extensive investment costs on equipment, while the yield rate may also be improved.

BRIEF DESCRIPTION OF THE DRAWINGS

FIG. 1 is a diagrammatic cross-sectional view showing an example of a device employed in the production process for coated powders of the present invention, taken along the direction of the flow channel of the gaseous water and oil repellant agent.

PREFERRED EMBODIMENTS

First Aspect

Preferably, the weight ratio of the water and oil repellant agent to the inorganic base powder is 1:0.005 to 1:0.50, the heating is at a temperature high enough to activate at least the inorganic base powder, and the water and oil repellant agent is preferably fluorosilane, fluorosilazane or fluorinated hydrocarbons.

Meanwhile, as means for providing the inorganic base powder with active sites, it has been contemplated that the base powder be coupled with a silane or titanium coupling agent to hydrolyze them, and the water and oil repellant agent be reaction-bonded, that is, bonded under reacted state, with the terminal OH group of the coupling agent.

However, with the use of, for example, the silane coupling agent, it is reactable with silica type inorganic powders, but is not reactable readily with titanium type inorganic powders. Conversely, with the use of titanium coupling agent, it is not reacted readily with the silica type inorganic powders. In the case of red oxides of iron, such as $Fe_2O_3$ or $Fe_3O_4$, suitable coupling agents cannot be found. Thus it is necessary to use different coupling agents for different inorganic base powders, or there is no suitable coupling agent, which is industrially inconvenient or unreasonable.

On the other hand, titanium oxide hydrate tends to co-exist stably with alkalis, but is unstable and tends to transform to oxides under ordinary conditions. Thus, for preparing stable titanium hydrate, it may be contemplated that titanium oxide be dissolved in potassium bisulfate, the resulting solution is heated from some distant point to free the solution of a sulfurous gas, and the resulting mass free of the sulfurous gas is heated to 900° C., cooled, added to by 5%-sulfuric acid, heated and added to by ammoniac water. This method is, however, industrially not advantageous because of pollution caused by waste gases and equipment problems. With the use of titanium tetrachloride, monomers, dimers or trimers of titanium oxide hydrate may be produced, so that titanium oxide hydrate of stable quality cannot be produced and unstable resultant states are entrained.

The present inventors have additionally found the above described technology and succeeded in completing the present invention.

As the inorganic base powders, inorganic pigments, other inorganic powders or mixtures thereof, may be employed.

The water and oil repellant agent is defined as the agent exhibiting both water repellancy and oil repellancy. Thus the agent generally exhibits affinity neither to oleophilic substances or to hydrophilic substances, while not exhibiting affinity to a mixture of the hydrophilic and oleophilic materials. More specifically, it may be exemplified by fluorosilane, fluorosilazane or fluorinated hydrocarbons. The fluorosilane includes perfluoro alkyl silane, fluorosilane having an urethane linkage, fluorosilane having its silicone part partially modified with fluorine or fluoride, etc. The fluorosilazane includes those represented by the general formula (2) hereinafter mentioned, e.g., perfluoro alkyl silazane. These water and oil repellant agents exhibit affinity to activated powders.

The water and oil repellant coated powders of the present invention has a coated layer or vapor deposition layer on the surface of the inorganic base powders, which layer is reaction-bonded at the reactive sites on the surface of the base powders. The water and oil repellant agent reaction-bonded to the active site on the surface of the inorganic base powders is not simply adhered or adsorbed to the powder surface, but is bonded strongly to and is not removed easily from the powder surface. Thus the coating layer or the vapor deposition layer is not removed from the inorganic base powders under the mechanical force, impact, centrifugal force or shearing force. The coating layer or the vapor deposition layer is formed by the water and oil repellant agent to prevent water, perspiration or sebum from intruding into the inorganic base powders. The water and oil repellant agent of the coating layer is bonded to the overall surface of the inorganic base powders in an amount sufficient to present such intrusion. The weight ratio of the coating layer is 1:0.005 to 1:0.50 part of the coating layer relative to 1 part of the inorganic base powders. The weight ratio of not more than 0.004 is occasionally insufficient to prevent the intrusion. Depending basically on the number of active sites possessed by the inorganic base powders, the upper limit of the weight ratio of ca. 0.50 is sufficient, since the water and oil repellancy is not improved markedly above the weight ratio of 0.50. This ratio is more preferably 1:0.08 to 1:0.45, and most preferably 1:0.11 to 1:0.40.

The coating layer and the vapor deposition layer is thermally decomposed at a temperature markedly higher than the boiling point of the water and oil repellant agent per se prior to being formed into the coating layer, there being no peak of heat absorption (which peak would be observed in case with simple affixture or adhesion to the inorganic base powders). Moreover, such coated powders are not deteriorated when agitated or allowed to stand in an aqueous system or various oily solvents.

Heating of the inorganic base powders in the method for producing the coated powders of the present invention is effective to render the acid and base points as the active sites for the surfacial reaction of the base powders more definite and to increase the number thereof as well as to radicalize the base powder surface.

The term "active site" means the state in which molecules are excited to a higher energy state due to electron surplus or deficit, due to electron segregation, ionization or radicalization, to promote the occurrence and progress of the chemical reaction, inclusive of the tripo plasma state giving rise to electron radiation or disorder in structure. For instance, when the inorganic base powders are titanium oxide powders, the active site means the state in which $TiO_2$ has been changed to $TiO^{2-}$ due to heating at 300° to 600° C. When the powders are sericite powders, the active site means the state in which it has been due to heating at 500° to 550° C., changed to:

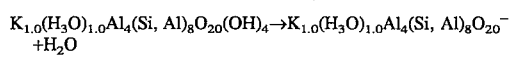

$$K_{1.0}(H_3O)_{1.0}Al_4(Si, Al)_8O_{20}(OH)_4 \rightarrow K_{1.0}(H_3O)_{1.0}Al_4(Si, Al)_8O_{20}^- + H_2O$$

The term "acid point" means the point at which the base powders, while remaining in the solid state, exhibit the properties as the Bransted acid, referred to as the Bronsted acid hereinafter, or as the Lewis acid. The base powders exhibit at this point the basically acidic action and either donate protons or receive electron pairs.

The term "base point" indicates the point at which the base powders exhibit solid basicity, that is, the properties as the Bronsted base or Lewis base, while the base powders remain in the solid state. At this point, the base powders exhibit a basically basic function and either receive protons or donate electron pairs.

The acid and base points are relatively determined by the magnitude of the force of chemical affinity.

The gaseous water and oil repellant agent easily undergoes a contact reaction with the inorganic base powders under heating and are bonded to the active sites on the base powder surface to form the vapor deposition layer coating the base powder surface. The heating temperature of the base powders may be suitably determined depending on the type of the base powders, so that the base powders are not deteriorated. When the base powders are titanium oxide, for example, they are heated to within the range of 300° to 600° C., preferably to 500° C. Titanium oxide has about 0.2 m mol/g of acid points around 500° C. and, when heated continuously, has the number of the Lewis acid points more than that of Bronsted acid point of titanium oxide. The Lewis acid points of titanium oxide are classified into those produced by desorption of molecular water and those by desorption of lone OH groups. The radicalization, i.e., turning into $TiO^{2-}$, of titanium oxide $TiO_2$, may also be performed in the above temperature range and preferably at 500° C. The white-colored titanium oxide is turned into yellow color like the color of sulfur at the above temperature range. This change into the yellow color is distinct from the phenomenon in which titanium oxide admixed with a minor amount of zinc is turned into light yellow and in which the titanium oxide turned into the yellow color is again turned, at lower than 300° C., into the original white color which is the color prior to heating, while titanium oxide admixed with zinc remains light yellow at ambient temperature. Hence, titanium oxide is believed not to have changed in structure before and after the heating in the above temperature range. The base powders having the aluminum silicate composition, such as sericite, are heated to within the range of 250° to 650° C., for maintaining their crystal structure and good feeling. It is because the results of thermal analyses have revealed that the adsorbed water starts to be removed at 100° to 200° C., the OH groups start to be freed (desorbed) above 500° C. and are completely freed at 700° C.

On the other hand, the base powders having the magnesium silicate composition, such as talc, are higher by several tens of degrees in the elimination temperature of the absorbed water, OH group desorption start temperature and the OH group desorption termination temperature than those having the aluminum silicate composition, so that they are heated to within the range of 300° to 700° C. for maintaining their satisfactory feeling.

As a preliminary step for activating the inorganic base powders, the latter may be treated with an acid or an alkali, depending on the solid acidity and basicity as well as on the acidity and basicity of the water and oil repellant agent. However, in this case, acids or alkalis of a higher concentration may become necessary depending on the kinds of the inorganic base powders employed. In this case, since problems are presented in connection with disposal of the alkaline waste liquid and acids of a higher concentration and environmental pollution, while production costs are also increased due to increase in production time, this method may not be an industrially advantageous method.

The gaseous water and oil repellant agent may be produced by vaporizing the water and oil repellant agent such as by heating. The heating temperature may be selected for example in the range from ambient temperature to 300° C., depending on the kind of the water and oil repellant agent. When contact-reacting the gaseous water and oil repellant agent with activated inorganic base powders, the gaseous water and oil repellant agent may be contact- reacted with the base powders either by itself or in conjunction with gases inert to the activated inorganic base powders.

It is thought that the water and oil repellant agent in combined wholly or partially with active sites of the inorganic base powders by the contact reaction between the active sites of the inorganic base powders and the gaseous water and oil repellant agent. For example, when the inorganic base powders are sericite $K_{1.0}(H_3O)_{1.0}Al_4(Si, Al)_8O_{20}(OH)_4$ (abbreviated as □-$(OH)_4$), or titanium oxide $TiO_2$, and the water and oil repellant agent is fluorinated hydrocarbons (abbreviated as □-$CCl_2F$), or fluorosilane

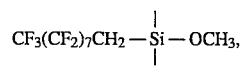

the reaction may presumably be schematized as follows:

(a) □-OH + $CCl_2F$ ⟶ □-Cl + $COCl_2$   (450° C.)
□-Cl + t-$CCCl_2F$ ⟶ □-F + $CCl_4$   (450° C.)
$COCl_2$ + $H_2O$ ⟶ HCl + $CO_2$
($H_2O$: water used as trap)

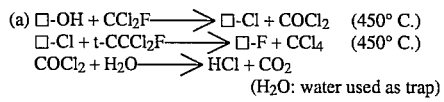

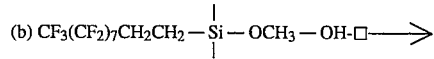

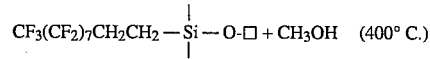

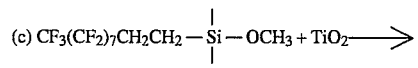

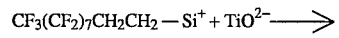

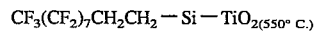

(d) If there be a small amount of $Ti(OH)_4$ having OH groups, the reaction formula is possibly similar to that for sericite, although the reaction is not the main reaction but of the secondary nature.

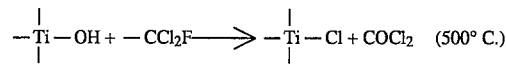

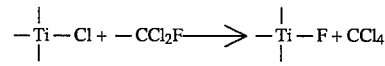

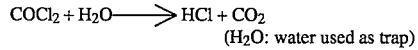

$COCl_2$ + $H_2O$ ⟶ HCl + $CO_2$
($H_2O$: water used as trap)

The contact reaction between the activated inorganic base powders and the gaseous water and oil repellant agent is preferably performed until completion of the reaction. The time involved in the contact reaction is 2 minutes to 3 hours, depending on the kind and the feed (rate or amount) of the water and oil repellant agent to the base powders. When the gaseous water and oil repellant agent is the fluorinated hydrocarbon, the more the number of fluorine atoms, the longer is the time which should elapse until completion of the contact reaction.

The amount of the coated powders in the makeup cosmetics may be 1.0 to 40.0 wt % for emulsion type, 0.5 to 30 wt % for oil gel type, 5 to 90 wt % for pressed type and 5 to 90 wt % for loose type. The coated powders may be used directory or in an amount of 100 wt % as the makeup cosmetics for facing powders, powdery eye shadow or dusting powders.

In preparing the coated powders of the present invention, when impurities are adhered to or apt to be adhered to the inorganic base powders, the latter are washed preferably sequentially with isopropyl alcohol, acetone or demineralized water and dried to remove the impurities before being used as the inorganic base powders.

A preferred method for producing the coated powders of the present invention is hereinafter explained by referring to the drawing. The sole FIGURE is a diagrammatic cross-sectional view of an illustrative device for producing the coated powders of the present invention, taken along the direction of the flow channel of the gaseous water and oil repellant agent. A quartz glass tube 2, having a circular cross-section orthogonal to the direction of the flow channel of the gaseous water and oil repellant agent, is provided with a gas inlet 2a, a gas outlet 2b and a valve 4. One or more types of inorganic base powders 1, preferably pre-treated by being washed sequentially with isopropyl alcohol, acetone and water and dried, has a portion thereof filled with the inorganic base powders clamped by an openable tubular electrical furnace 3, produced by the Ishizuka Denki Seisakusho K.K., and the furnace 3 is set to 250° to 650° C. The gaseous water and oil repellant agent is then supplied at a temperature ranging room ambient temperature to 300° C. at the inlet 2a of the quartz glass tube, at a rate of 0.1 to 10 lit/min, together with a carrier gas within the range of 0.2 to 10 lit/min, for 2 minutes to 3 hours, to effect contact reaction between the inorganic base powders and the gaseous water and oil repellant agent. The reaction product is then cooled to a temperature close to the ambient temperature to produce desired coated powders.

The inorganic pigments employable in the coated powders of the present invention are preferably of a mean particle size of 0.01 to 10 μm and may include inorganic color pigments with various colors, pigments with pearly luster, metal powders or the like. The inorganic pigments may be exemplified by inorganic white pigments, such as titanium oxide or zinc oxide, inorganic red pigments, such as iron oxides (red oxide of iron) or iron titanate, inorganic yellow pigments such as yellow iron oxide or yellow ochre, inorganic purple pigments, such as Mango violet or cobalt violet, inorganic green pigments such as chromium oxide, chromium hydroxide or cobalt titanate, inorganic blue pigments such as ultramarine or Perusian blue, pearly luster pigments such as titanium oxide-coated mica, titanium oxide-coated bismuth oxychloride, bismuth oxychloride, titanium oxide-coated barium sulfate, titanium oxide-coated talc, guanine or colored titanium oxide coated mica, and metal powder pigments such as aluminum or copper powders.

As other inorganic powders, those having the mean particle size of 0.1 to 20 μm are preferred. There is no limitation to these powders as long as they may be used in cosmetics. Examples of these powders include inorganic powders of talc, Kaolin, sericite, muscovite, synthetic mica, phlogopite, lepidolite, biotite, vermiculite, magnesium carbonate, calcium carbonate, diatomaceous earth, magnesium silicate, calcium silicate, aluminum silicate, barium silicate, strontium silicate, metal salts of tungstenic acid, α-iron oxide, iron oxide hydrate, silica or hydroxyapatite. For producing outstanding results is smoothness in spreading, ease in spreading and in preventing the caking, spherical powders are preferably selected and used preferably in an amount of 1 to 30 wt % based on the total amount of the base powders. When two or more of the above materials are used, they are preferably previously pulverized, mixed and dispersed by a pulverizer.

The fluorosilane, such as perfluoro alkyl silane or perfluoro alkyl silazane, applied to the water and oil repellant agent of the coating layer, is represented by the following general formulas (1) and (2) respectively:

General formula (1):

$$CF_3(CF_2)_nCH_2-CH_2Si-R_3$$

(n=0 to 10)

or $$(C_nF_{2n+1})_mCH_2-CH_2Si-R_3$$

(n=1 to 5 m=1 to 10, $R_3$=H, OH, alkoxy group ($OCH_3$ etc.) or phenyl group ($OC_6H_5$))

General formula (2):

(i) $Rf-Si(NH_2)_3$

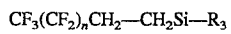

(ii) $Rf-Si(NH_2)_2-NH-Si(NH_2)_2$
$\quad\quad\quad\quad\quad\quad\quad\quad\quad\quad |$
$\quad\quad\quad\quad\quad\quad\quad\quad\quad\quad Rf$ (dimer of (i))

General formula (2): -continued

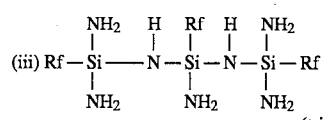

(iii) $Rf-Si(NH_2)(NH_2)-N(H)-Si(Rf)(NH_2)-N(H)-Si(NH_2)(NH_2)-Rf$ (trimer of (i))

(iv) (oligomer of (i))

Where, $Rf=F+CF(CF_3)-CF_2-O\frac{}{n}$     (n = 1 to 10)
or $Rf=C_nF_{2n+1}-$     (n = 1 to 10)
or $Rf=F+CF_2-CF_2-O\frac{}{n}$     (n = 1 to 10)

The fluorosilane having the urethane linkage may be represented by the formula (3):

General formula (3)

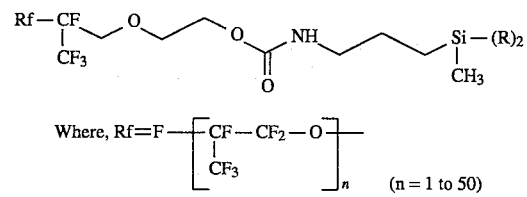

Where, $Rf=F-\left[\begin{array}{c}CF-CF_2-O\\|\\CF_3\end{array}\right]_n-$ (n = 1 to 50)

R=hydrogen atom, phenyl group, hydroxy group or alkoxy group ($OCH_3$, $OC_2H_5$, $OC_3H_7$, $OC_4H_9$).

On the other hand, fluorosilane having its silicone part partially modified with fluorine or fluoride, is represented by the following formula (4):

General formula (4)

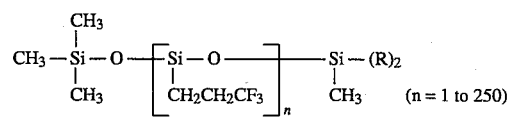

(n = 1 to 250)

or

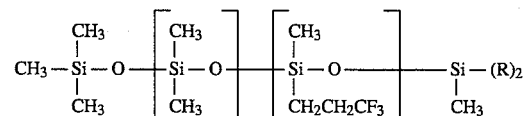

(m = 0 to 70, n = 1 to 30)

Where R has the same meaning as in the above formula (3).

The compounds represented by the above general formulae include not only those having straight chains, but also those having branched chains and optical isomers.

The fluorinated hydrocarbon compounds include methane type or ethane type compounds. The methane type compounds are such as monochloro trifluoromethane (Freon-11), dichloro difluoromethane (Freon-12), monochloro difluoromethane (Freon-22) or trifluoromethane (Freon-23), and the ethane type compounds are such as trichloro trifluoroethane (Freon-113), dichloro tetrafluoroethane (Freon-114), monochloro pentafluoroethane (Freon-115), dichloro trifluoroethane (Freon-123) or tetrafluoroethane (Freon-134A).

Second Aspect

Preferably, the coated powders provided with a baked coating first layer (coated and heat-treated first layer) stated in (2-2) and (2-3) are produced by the method of (2-1) above, the primer is the Lewis acid or Lewis base and the activated inorganic base powders are produced by grinding (or milling). The "baked coating layer" denotes the coating layer resulting from thermal the composition of the applied layer on the inorganic base powder through the heat treatment.

Although the activated inorganic base powders may also be produced by heating, plasma processing, hydrothermal reaction, etching with an acid or an alkali or introduction of functional groups, they may be produced advantageously by grinding in view of industrial production.

Meanwhile, as means for providing the inorganic base powders with active sites for coupling the inorganic base powders with the water and oil repellant agent, there is known a method consisting in coupling a silane coupling agent or a titanium coupling agent with the base powders, hydrolyzing the resulting product and coupling-reacting the water and oil repellant agent with the terminal hydroxy group of the coupling agent. As already described in the first aspect, this method is industrially inconvenient and unreasonable in that it is necessary to change the surf ace treatment agent for each of different types of the inorganic base powders, or there lacks a suitable coupling agent for certain inorganic powders.

There is also known a method consisting in etching the surface of the inorganic base powders as a pre-treatment of activating the base powder surface, a number of days are required for reaction until the reaction pH range is brought to the neutral pH range after the reaction. Above all, precipitation and hence decantation becomes extremely difficult to execute near the isoelectric point of the inorganic base powders. Thus the problems are presented that filtration is difficult to execute from the industrial point of view and that the yield is lowered due to repetition of the decantation.

In addition, titanium oxide hydrate is beset with inconveniences in connection with production, equipment and product instabilities.

The same considerations as those mentioned in the first aspect above apply for the second aspect.

The reactive auxiliary agent, when coated and heat-treated (i.e., baked) on the inorganic base powders along with the water and oil repellant agent, is reacted and combined with the base powders to promote and strengthen the bonding of the water and oil repellant agent to the base powders, while being reacted and combined with the water and oil repellant agent to promote the bonding of the water and oil repellant agent to the base powders (with or without the intermediary of the auxiliary agent) and filling the space between the particles of the water and oil repellant agent bonded to the base powders to render the coating layer more dense and compact by cross-linking.

These auxiliary agents may be exemplified by organic titanate, aluminum alcholate, aluminum chelate and cyclic aluminum oligomers.

The primer is a catalyst acting as the reaction initiator and promotor and not present or left over in the baked coating layer. Above all, the primer means the substance acting on the terminal functional groups of the water and oil repellant agent and charge the latter to a positive polarity to promote the reaction with the activated inorganic base powder surface, and attacking lone electron pairs of oxygen atoms of titanium oxide as the inorganic base powders not substantially having functional groups to localize the location of the electrons to render the usually unreactive inorganic base powders more reactive. The primer may be exemplified by Lewis acids or Lewis bases.

The heat treatment (baking) means bonding the constituents of the coating layer, such as the water and oil repellant agent, reactive auxiliary agent and oily agents with the inorganic base powders strongly to cross-link the constituents of the coating layer bonded to the inorganic base powders to produce a complex network structure. As for the second coating layer, the heat treatment (baking) means bonding each constituent of the coating layer with each constituent of the first coating layer as well as to cross-link the constituents per se of the second coating layer connected to the first coating layer for forming the complex network structure.

The baked coating layer applied to the inorganic base powders has both the water and oil repellancy by the presence of the water and oil repellant agent.

The activated inorganic base powders can be advantageously obtained by grinding and, since the base powder surface is activated, the sol id acid and base points are rendered explicit. Hence, coating the activated inorganic base powders with one or both of the water and oil repellant agent and the oily agent and with the reactive auxiliary agent without heat treatment is effective to raise the interaction between each of the water and oil repellant agent and the reactive auxiliary agents and the active point and functional groups of the base powders. In this manner, the coating layer not undergoing heat treatment is well adhered to the surface of the inorganic base powders. The primer promotes the above reaction.

The coated powders produced in accordance with the present invention are provided with an extremely tough baked (or cured) coating layer due to the synergistic action of (a) strong bonding between the constituents of the coating layer comprised of the water and oil repellant agent and the reactive auxiliary agent with or without oily agents; (b) the interaction between the constituents of the coating layer and the active sites and the functional groups of the inorganic base powders; and (c) the force of adhesion or adsorption of the coating layer constituents to the inorganic base powders. The surface activation of the inorganic powders is rendered possible by grinding such as with a ball mill, especially a ball mill operating at a lower rotational speed, tower mill or attrition mill.

The coated powders of the present invention exhibiting water and oil repellancy is provided on the powder surface with a heat-treated coating layer which has been rendered more dense and compact under the effect of cross-linking reaction of the water and oil repellant agent and the oily agent and/or the reactive auxiliary agent reaction-bonded to the surface functional groups and active sites the surface of the inorganic base powders. The water and oil repellant agent reaction-bonded to the reaction site on the surface of the inorganic base powders is not simply adhered or adsorbed to the powder surface, but is bonded strongly to and is not removed easily from the surface. Thus the coating layer or the vapor deposition layer is not removed from the inorganic base powders under the mechanical force, impact, centrifugal force or shearing force. The coating layer or the vapor deposition layer is formed by the water and oil repellant agent to prevent water, perspiration or sebum from intruding into the inorganic base powders.

The coating amount of the water and oil repellant agent, oily agent, reactive auxiliary agent and the primer on the activated inorganic base powders prior to heat treatment may be suitably set so that the above described intrusion may be prevented after the heat treatment. For example, in case of the inorganic base powders—water and oil repellant agent—primer combination, the weight ratio of the base powders: water and oil repellant agent: primer is 1:(0.004 to 0.50):(0.001 to 0.25), preferably 1:(0.1 to 0.47): (0.01 to 0.14) and most preferably 1:(0.15 to 0.30):(0.05 to 0.10). When the reactive auxiliary agent is additionally employed, the weight ratio of the inorganic base powders: water and oil repellant agent: primer: reactive auxiliary agent is 1:(0.004 to 0.50):(0.001 to 0.25):(0.01 to 0.3), preferably 1:(0.1 to 0.47):(0.01 to 0.14):(0.003 to 0.14), and most preferably 1:(0.15 to 0.30):(0.05 to 0.10):( 0.01 to 0.09).

The weight ratio lower than the above value is insufficient in many cases to prevent the above described intrusion from occurring. While the upper limit of the weight ratios basically depends on the surfacial functional groups of the inorganic base powders, surfacial active sites and the strength thereof, the water and oil repellancy is not meaningly improved even when the above weight ratio is exceeded, so that the above defined weight ratio suffices.

As for the effect of the presence or absence of the reactive auxiliary agent, the base powders not containing the reactive auxiliary agent may be allowed to stand for about six months in the state of being immersed in various oily agents or solvents for cosmetics, without undergoing deterioration, so that sufficient water and oil repellancy may be maintained. However, for affording the water and oil repellant effects to the powders for longer than the above period, the reactive auxiliary agents may be employed advantageously. In other words, stronger and more compact films may be formed by using the reactive auxiliary agent and the resulting coated powders remain stable and do not undergo deterioration for prolonged time when allowed to stand in an aqueous system or a variety of oily agents or solvents.

The above described means for producing the activated inorganic base powders in the production process of the present invention, including grinding, render the acid and base points as the active sites of the reaction on the base powder surface more conspicuous while increasing their number and rendering the base powder surface more radical.

As mentioned in the first aspect, the active sites mean the state of electron surplus or deficit such as electron segregation, ionization or radicalization, with the molecules being excited to higher energy states and being more apt to undergo chemical reactions, inclusive of generation of fresh surfaces of inorganic base powders, tripo plasma states causing disorder of structure or electron radiation.

For example, it is presumed that the following three structures (1), (2) and (3) are partially contained in the structure of titanium oxide:

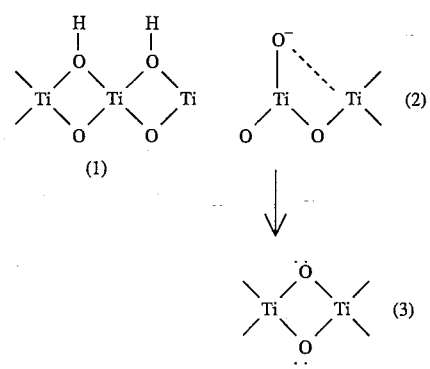

As for the reaction schema and, as an example, in the reaction with $CF_3(CF_2)_7CH_2.CH_2Si(OCH_3)_3$ as the fluorine type water and oil repellant agent, it is thought that $OCH_3$ in the fluorine type water and oil repellant agent react with OH to yield $CH_3CH$ in (1), the $O^-$ portion reacts with $OCH_3$ in (2), and $BF_3$ of the Lewis acid attacks to localize the electron location to increase the reactivity with the fluorine type water and oil repellant agent thereat, with the covalent bond being the main form of bonding.

In the case of sericite, the main reaction is that between OH of $K_{1.0}(H_3O)_{1.0}Al_4(Si, Al)_8O_{20}(OH)_4$ and $OCH_3$ of the fluorine type water and oil repellant agent, with electron localization occurring on the sericite surface due to grinding to produce electrical charges.

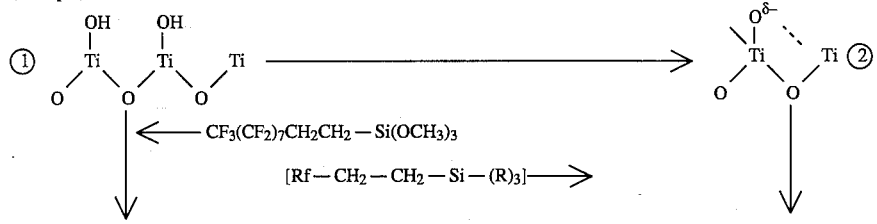

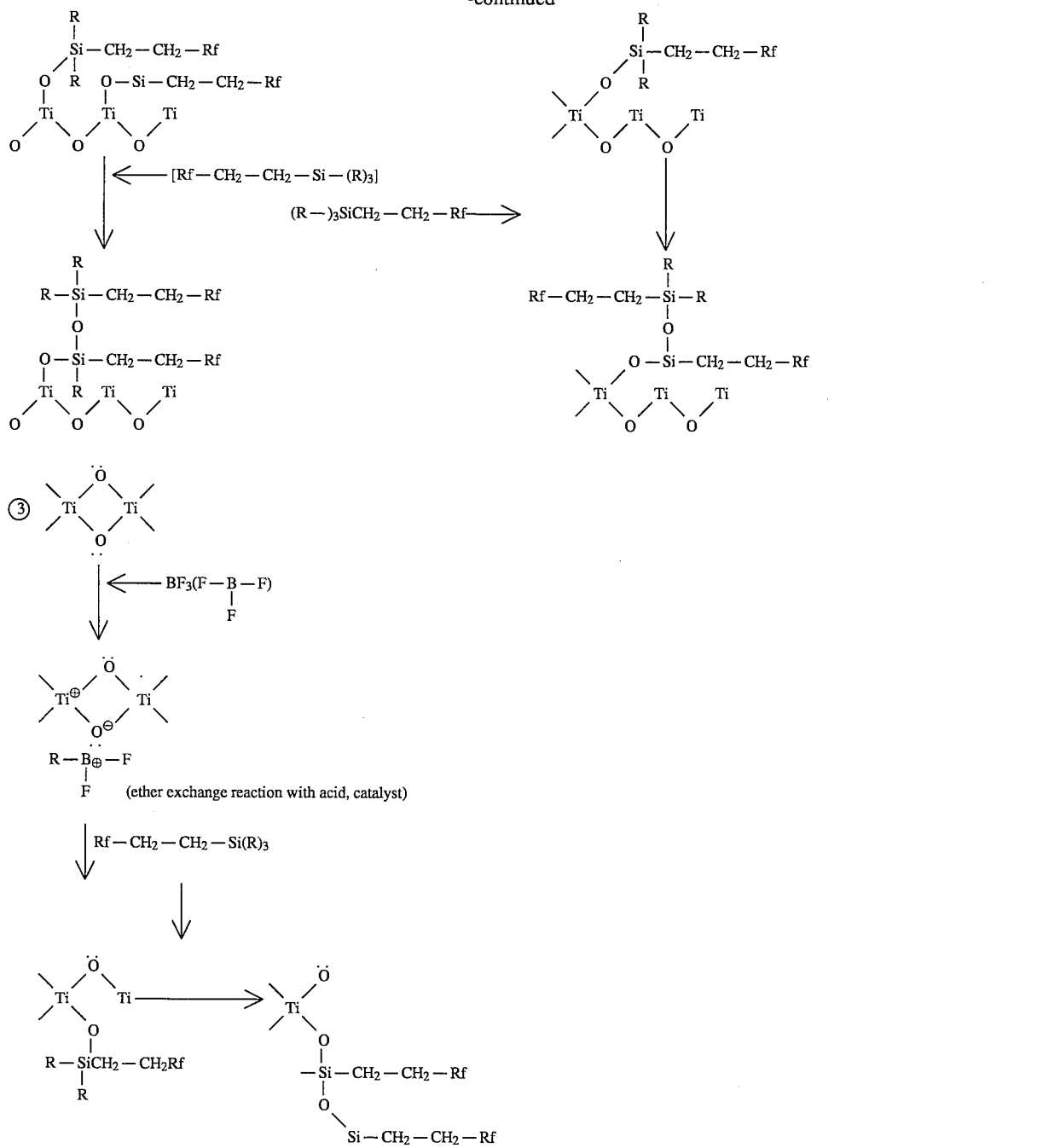

The acid point is as defined in the first aspect.

In the case with the water and oil repellant agent, it is contemplated that the reaction proceeds between the surface of the inorganic base powders activated by, for example, grinding and —Si(OCH$_3$)$_3$ and between the surfacial functional groups and OCH$_3$ of Si—(OCH$_3$)$_3$ and that heat treatment results further in the alcohol elimination reaction between OCH$_3$ of Si—(OCH$_3$)$_3$ to promote the reaction between the network among the fluorine based water and oil repellant agents, the solid surface (the inorganic base powder surface) and the fluorine based water and oil repellant agents to render the reaction between the network and the inorganic base powders more complete.

When the reactive auxiliary agents are used additionally, these agents cause a cross-linking reaction between the fluorine base water and oil repellant agents, additionally to the alcohol-eliminating reaction of the Si—(OCH$_3$)$_3$ groups, to provide formation of a stronger and more compact film.

The inorganic pigments applicable to the inorganic base powders in the second aspect of the present invention are the same as described in the first aspect.

The other inorganic powders are preferably of the mean particle size of approximately 1.0 to 20 μm. Any of the inorganic powders as exemplified in the first aspect may be employed as the other inorganic base powders.

The fluorosilane applicable in the second aspect is the same as those represented by general formula (1)–(4) exemplified in the first aspect.

The organic titanates of the reactive auxiliary agent may include organic compounds of titanium, or aluminum or the like. The organic compounds of titanium include tetra-i-propyl titanate (TPT), tetra-n-butyl titanate (TBT), butyl titanate Gimer (DST), tetrastearyl titanate (TST), triethanolamine titanate (TEAT), titanium acetyl acetate (TAA), titanium ethyl acetoacetate (TEAA), titanium lactate (TLA), tetraoctylene glycol titanate (OGT), di-n-butoxy-bis (triethanol aminato) titanium, TST polymer (n=2 to 10) and TFT polymer (n=10). The compounds of aluminum includes alcoholates, chelates or cyclic oligomer of aluminum. The aluminum alcoholate may include aluminum ethylate, aluminum isopropylate, mono-sec-butoxy isopropylate and aluminum sec-butylate; the aluminum chelates may include ethyl aceto acetate-aluminum diisopropylate, aluminum tris (ethylacetoacetate), alkyl acetcacetate diisopropylate, aluminum tris (acetylacetonate) and triethylaluminum; and the cyclic aluminum oligomers may include cyclic aluminum oxide isopropylate.

The primers may include Lewis acids such as boron trifluoride or complexes thereof (boron trifluoride ethyl ether complexes), nitrogen trifluoride, aluminum chloride, chloride or iron chloride (I), Lewis bases such as tetra-n-butyl ammonium bromide, and alkoxides or alcoholate obtained by substituting metal elements (Na, K, Ca, Al etc.) for H in OH-group of alcohol (methanol, ethanol etc.), e.g., sodium methoxide or the like.

As the oily agents, the oily agents generally applicable to cosmetics as starting materials that are not hydrophilic and that are water repellant, may be employed, and may include various hydrocarbons, higher fatty acids, oils and fats, higher alcohols and waxes, such as, for example, squalane, liquid paraffin, vaseline, microcrystalline wax, ozokerite, ceresin, myristic acid, palmitic acid, stearic acid, oleic acid, isostearic acid, cetyl alcohol, oleyl alcohol, 2-octyl dodecyl myristate, 2-octyl dodecyl gum ester, 2-octyl dodecyl avietate, 2-octyl dodecyl oleate, isopropyl myristate, isostearic acid triglyceride, coconut oil fatty acid triglyceride, olive oil, avogado oil, bees wax, myristyl myristate, transesterification oil of olive oil and castor oil, mink oil, or lanolin.

As the pre-treatment, the inorganic base powders are preferably washed sequentially with isopropyl alcohol (referred to as IPA hereinafter), acetone and water and dried to remove the contamination or water deposited on the inorganic base powder surface. The heating temperature for activating the inorganic base powders in case of normal pressure heating is preferably in the range from 80° to 1000° C., depending on the structural stability of the inorganic base powders.

The following points are noteworthy herein:
(i) The composition of the water and oil repellant agent with or without the reactive auxiliary agent constituting the coating layer before heat treatment is selected to be within a range necessary to coat the inorganic base powders as the core completely after heat treatment. The composition range lower than the above specified range is insufficient to give satisfactory results, while that higher than the above specified range is not effective to give any further improvement thus of no merits to use such amount.
(ii) It is not desirable to perform heat treatment of the water and oil repellant agent alone, that is, without the primer, on the activated inorganic base powders, since the water and oil repellant agent is bonded strongly with the inorganic base powders, but a large number of particles of the water and oil repellant composition remain uncombined with the base powders, such that the denseness of the film interposed between the particles of the water and oil repellant agent, that is, the denseness of the heat treatment layer is extremely low, or the particles of the water and oil repellant agent remain nearly uncombined, thus the wetting proceeds with lapse of time. However, by applying the primer, such as Lewis acid or base, to the reaction between the surfaces of the inorganic base powders and the water and oil repellant agent, the reaction (bonding reaction) proceeds more smoothly, while the reaction between the particles of the water and oil repellant agent is accelerated. When heat treatment is performed without activation and without using the primer, the above state becomes worse and the thus treated base powders do not take part in preventing the unevenness of makeup finish.
(iii) When the water and oil repellant agent and the reactive auxiliary agent with or without oily agents as the constituents of the coating layers are simply coated on the unactivated inorganic base powders, that is, without heat treatment, or when the moisture exists in the base powders in more than a required amount such that the reactive auxiliary agent when used undergoes hydrolysis without taking part in the cross-linking reaction, and the heat treatment is not performed, the inorganic base powders and the constituents of the coating layer remain practically uncombined without conferring any desirable influences on the durableness of the cosmetic effect.
(iv) When the inorganic base powders are not activated, as mentioned at (ii) or (iii) hereinabove, the coating layer before the heat treatment is simply adhered or adsorbed to the surfaces of the base powders, while there lacks an interaction between the inorganic base powders and the constituents of the coating layer, with the result that these constituents may be easily freed from the surfaces of the inorganic base powders under the mechanical force, centrifugal force, shearing force or impact, so that the desired product is not produced.
(v) The temperature of the heat treatment is basically the temperature which is lower than the boiling point of the water and oil repellant agent (at the state before heat treatment) and at which the water and oil repellant agent is not decomposed, volatalized or deteriorated. With the use of the reactive auxiliary agent, it is preferably the temperature at which the reaction of the reactive auxiliary agent and that of the fluorine base water and oil repellant agent proceed smoothly. The heat treatment temperature is usually in the range from 80° C. to 200° C. The heat treatment time, which is the time necessary to complete the complex reactions between the constituents themselves before the heat treatment and between the base powders and constituents, is usually 1.5 to 48 hours. The heat treatment longer than this time interval is unnecessary for completing the reactions, while that shorter than the time interval is ineffective to perform heat treatment to acquire the targeted strength of the coating film and cosmetic effects.

The amount of the present coated powders in the makeup cosmetics may be 1.0 to 40.0 wt % for emulsion type, 0.5 to 30 wt % for oil gel type, 15 to 90 wt % for pressed type and 10 to 90 wt % for loose type. The coated powders may be used directly or in an amount of 100 wt % as the makeup cosmetics for face powders, powdery eye shadow or dusting powders.

For producing the coated powders of the present invention, the following methods are preferably employed.

First Method

The pre-treatment step for the inorganic base powders, that is, the step of sequentially washing the inorganic base powders with IPA, acetone and demineralized water and drying the washed product is not indispensable to the invention and performed preferably. The inorganic base powders that have or have not passed through this pre-treatment are mixed into a solution consisting of an organic solvent in which the water and oil repellant agent and the primer are dissolved, the resulting mixture is stirred, subjected to grinding and heat treating after removal of the organic solvent and, if necessary, the resulting mass is washed with an organic solvent, dried and pulverized to produce the desired coated powders.

Second Method

The inorganic base powders, preferably pre-treated in the above described manner, are mixed into an organic solvent containing the water and oil repellant agent, primer and the reactive auxiliary agent, stirred, subjected to grinding, heat treated after distilling off the organic solvent, taken out, washed with an organic solvent if necessary, dried and pulverized to produce the targeted coated powders.

The organic sol vents employed in the above steps include xylene, toluene, benzene, n-hexane, butanol, isopropyl arcohol, ethyl acetane, methylethylketone, methylisobutylketone, petroleum ether, chloroform, Freon 112, Freon 113 and Freon 12.

An example of the method for producing the coated powders according to the second aspect of the present invention is described in detail hereinbelow. In the following, parts indicate those by weight, unless specified otherwise.

First Method 100 parts of one or more kinds of the inorganic base powders, (preferably washed with IPA, ace tone and water and dried through a pre-treatment, hereinafter the same), are mixed in a solution in which 100 to 800 parts of the organic solvent, 0.4 to 50 parts of the water and oil repellant agent and 0.1 to 20 parts of the primer were previously dissolved, mixed, stirred and subjected to grinding at not higher than 110° C. for 1 to 48 hours and the organic solvent is distilled off (optionally further dried). The water and oil repellant agent and the primer are coated on these base powders as the cores. Heat treatment is then performed at 80° to 200° C. for 1.5 to 48 hours (primer disappearing simultaneously and the heat-treated product is then cooled or the temperature is then reset to the ambient temperature to produce the desired coated powders. If necessary, the step of washing with the organic solvent may be performed after the heat treatment to remove the residual primer, if any, and the resulting product may then be dried to produce the coated powders.

Second Method 100 parts of one or two or more kinds of the inorganic base powders are mixed in a solution in which 100 to 800 parts of the organic solvent, 0.4 to 50 parts of the water and oil repellant agent, 0.1 to 20 parts of the primer and 1 to 30 parts of the reactive auxiliary agent were previously dissolved, mixed, stirred and ground at not higher than 110° C. for 1 to 48 hours and the organic solvent is distilled off (and further optionally dried). The water and oil repellant agent and the reactive auxiliary agent are coated together with the primer on these base powders as the cores. Heat treatment is then performed at 80° to 200° C. for 1.5 to 48 hours simultaneously removing the primer. The heat-treated product is then cooled or the temperature is then reset to the ambient temperature to produce the desired coated powders. If necessary, the step of washing with the organic solvent may be performed after heat treatment to remove the residual primer, if any, and the resulting product may then be dried to produce the coated powders.

In the above described coated powders, the starting material manifesting higher water and oil repellancy and occasionally the reactive auxiliary agent are formed into a film tightly bonded to the base powders under the interaction produced by the grinding operation of the inorganic base powders and the heat treatment, so that the base powders are not affected directly by oil or moisture. Also the film strength is increased by the heat treatment so that the powders can withstand the crushing or grinding force satisfactorily, while no change is caused in the wetting property to the powders of the pigments, with the result that unevenness or makeup dry of makeup finish can be prevented completely from occurring.

From the results of thermogravimetric analysis, differential thermogravimetric analysis, differential thermal analysis, and the analysis of the moisture produced on heating, it may be inferred that, since the thermal decomposition point indicated by the exothermic peak of the coated powders exists at a temperature much higher than the boiling point of the water and oil repellant agent, and there is no endothermic absorption peak in the vicinity of the boiling point due to weak adherence or bonding, the coated powders manifest strong chemical bonding.

Also, as described hereinabove, the etching process with an acid or an alkali is unnecessary to perform in the present process and hence the significant saving in the production time may be achieved due to the resultant elimination of the decantation process. Although it is known to effect heating for activating the powders, as for example by directly dipping the heated base powders in an organic solvent containing the water and oil repellant agent, this method is not necessarily advantageous for industrial application because of the considerable investment required in the industrial equipment. Grinding is highly meritorious for industrial application since the inorganic base powders may be activated at normal temperature and pressure with the use of machines and apparatus of the well-known type.

It suffices that the baked coating layer coating the inorganic base powders completely covers the outer periphery of the inorganic base powders in intimate and tight contact with the base powder surface, while it is not necessary for the coating layer to cover the inorganic base powders to a uniform thickness.

In the following, the preferred embodiments of the present invention are further elucidated by reference to the Examples.

EXAMPLES

EXAMPLE 1-1

Powder Foundation 175 parts of IPA were added into 50 parts of sericite, and the resulting mass was stirred for 60 minutes, washed with 85 parts of acetone and 175 parts of demineralized water and dried at 50° C. for 4 days. 50 parts of the thus pre-treated sericite were charged into a quartz glass tube 30 mm in diameter, which was then placed in an openable tubular electrical furnace. As the temperature within the furnace reached 500° C., 1,2,2 trichloro-1,1,2 trifluoroehane (Freon 113) gas was supplied into the quartz glass tube at a flow rate of 3.0 lit/min to effect contact reaction for 7 minutes. The supply of the gas was then discontinued and the contents of the furnace were cooled to ambient temperature and taken out to produce the coated powders Ia of the present invention.

When titanium oxide was used in place of sericite, the process similar to the above described process was carried out except effecting the contact reaction for 30 minutes at the temperature within the furnace of 450° C. to produce the coated powders Ib of the present invention.

| (A) | coated powders Ia | 53 parts |
| --- | --- | --- |
| | coated powders Ib | 10 parts |
| | talc | 15 parts |
| | spherical magnesium silicate | 4 parts |
| | magnesium stearate | 2 parts |
| | red oxide of iron | 4 parts | was mixed together and stirred for one minute by a Henschel mixer and subsequently pulverized in a pulverizer. The pulverized product was transferred to the Henschel mixer to which the following composition B was added:

| (B) | squalane | 7.8 parts |
| --- | --- | --- |
| | cetyl 2-ethyl hexanoate | 4 parts |
| | perfume | 0.2 parts |

The mixture was mixed and stirred for 10 minutes, taken out, homogenized by a blower sifter and charged into a container to a powder foundation product.

EXAMPLE 1-2

Powder Eye Color 40 parts of titanium oxide, 30 parts of white mica, 4 parts of red oxide of iron and 4 parts spherical silica were charged into 300 parts of IPA, and the resulting product was washed with 200 parts of acetone, washed three times with 400 parts of demineralized water and dried at 40° C. for three days. 30 parts of the thus produced dried powders were charged into a quartz glass tube 30 mm in diameter which was then placed in an openable tubular electrical furnace. As the temperature in the furnace reached 430° C., Freon 113 gas containing 2% perfluoroalkylsilazane (8 fluorine atoms) was introduced into the glass tube at a flow rate of 6.1 lit/min mixed with the nitrogen gas at 4.2 lit/min to effect a contact reaction for 40 minutes. The gas supply was then discontinued, and the reaction mass was cooled to ambient temperature and taken out to produce the coated powders II of the present invention.

The following composition A:

| (A) | coated powders II | 87 parts |
| --- | --- | --- |
| | titanium oxide-coated talc | 4 parts | was mixed for one minute in a Henschel mixer and pulverized in a pulverizer. The pulverized product was transferred into a Henschel mixer, and added thereto was the following composition B:

| (B) | dimethylpolysiloxane | 4.8 parts |
| --- | --- | --- |
| | isostearyl alcohol | 2.0 parts |

-continued

| | squalane | 2.0 parts |
| --- | --- | --- |
| | perfume | 0.2 parts |

The resulting mass was mixed together for 8 minutes, taken out, homogenized in a pulverizer and charged into a container resulting in a product.

EXAMPLE 1-3

Foundation 50 parts of titanium oxide, 30 parts of red oxide of iron and 20 parts of talc were mixed and dried into 50° C. for four days. 50 parts of the thus dried powders were charged into a quartz glass tube 30 mm in diameter which was then placed in an openable tubular electrical furnace. As the temperature within the furnace reached 500° C., perfluoro alkylsilane $(CF_3.CH_2.CH_2.Si(OCH_3)_3)$ in a vapor form was supplied at 180° C. at a flow rate of 4.2 lit/min together with a helium gas at 4.2 lit/min to effect a contact reaction for 1.5 hours. The gas supply was then discontinued and the reaction mass was cooled to ambient temperature and taken out to produce the coated powders III of the present invention.

The following composition A:

| (A) | coated powders III | 20 parts |
| --- | --- | --- |
| | stearic acid | 1.0 parts |
| | cetanol | 2.0 parts |
| | squalane | 8.0 parts |
| | octyldodecyl oleinate | 3.0 parts |
| | lanoline | 3.0 parts |
| | surfactant | 5.0 parts |
| | butyl paraben | 0.1 parts |
| | methyl paraben | 0.1 parts | and the following composition B:

| (B) | propylene glycol | 2.0 parts |
| --- | --- | --- |
| | glycerine | 4.0 parts |
| | thickener | 1.5 parts |
| | demineralized water | 49.4 parts | were separately dissolved and kept at 80° C. The composition B was gradually added to the composition A and the resulting mixture was stirred thoroughly and emulsified. On termination of emulsification, the following composition C:

| (C) | perfume | 1.0 part |
| --- | --- | --- | was added to the reaction mass and the resulting product was stirred at 80° C. for three minutes, cooled with water to 40° C., taken out and charged into a container resulting in a product.

Comparative Experiments

The coated powders produced by the method of the present invention and the conventional cosmetic composition were compared based on the qualitative evaluation of the water and oil repellant properties.

Samples (a) coated powders Ia of Ex. 1-1 of the present invention
(b) coated powders Ib of Ex. 1-1 of the present invention
(c) coated powders II of Ex. 1-2 of the present invention
(d) coated powders III of Ex. 1-3 of the present invention
(e) cosmetic powders surface-treated with a fluorine base resin according to the JP Patent Kokoku No. 61-48803/1986
(f) cosmetic powders treated with a fluorine-containing water and oil repellant agent according to the JP Patent Kokoku No. 61-55481/1986
(g) a mixture of sericite and 1,2,2 trichloro-1,2,2 trifluoroethane Experimental Procedure 5 g of various oily agents (squalane, oleic acid, isostearyl alcohol and cetyl 2-ethyl hexanoate and demineralizee water were weighed out into a test tube into which 0.1 g of the samples was introduced and which mixture was shaken at ambient temperature 100 times, allowed to stand for two days, again shaked 100 times and allowed to stand at ambient temperature for two days for evaluation.

In preparing the samples (a) to (d), the products obtained in Example 1-1 to 1-3 were taken out and each 20 g of the products was dispersed in 200 g of xylene, stirred for 30 minutes in a magnetic stirrer, taken out, filtered, dried for 24 hours in a dryer maintained at 50° C., taken out and pulverized to samples.

The results of the experiments are shown in Table 1.

TABLE 1

|     | water | squalane | oleic acid | isostearyl alcohol | cetyl 2-ethyl hexanoate |
| --- | --- | --- | --- | --- | --- |
| (a) | A | A | A | A | A |
| (b) | A | A | A | A | A |
| (c) | A | A | A | A | A |
| (d) | A | A | A | A | A |
| (e) | C | X | X | X | X |
| (f) | C | X | X | X | X |
| (g) | X | X | X | X | X |

A . . . The powders are accumulated in their entirety on the gas-liquid interface and the solvent remains transparent
B . . . The powders are accumulated on the gas-liquid interface but are partially precipitated on the bottom of the test tube; the solvent remains transparent
C . . . Only a very small portion of the powders remain on the gas-liquid interface, while the majority thereof are precipitated on the bottom of the test tube and the powders are partially dispersed in the solvent
X . . . The totality or majority of the powders are precipitated and the powders are dispersed to a great extent in the solvent From the thermogravimetric analysis, differential thermogravimetric analysis, differential thermal analysis and analysis of water produced on heating, it may be inferred that the product manifests strong chemical bonding. This is because (a) the thermal decomposition point of the coating layer on the powder surface exists at a much higher temperature than the boiling point of the water and oil repellant agent per se, (b) there is no heat endothermic peak which is usually observed in the vicinity of the boiling point of the water and oil repellant agent due to the weak bonding of the water and oil repellant agent with the inorganic base powders, and (c) when shaked severally in the aqueous system or in various oily agents, the coated powders of the present invention accumulate on the gas-liquid interface without being deteriorated with lapse of time.

In the JP Patent Kokoku Nos. 61-48803/1986 and 61-55481/1986, the surface treatment process is applied at an extremely low surface activity to limited hydroxy groups in the clay minerals in the inorganic base powders which are not made in the activated state. On the other hand, titanium oxide and mica titanium containing it are practically devoid of hydroxy groups and at most contain only a trace amount of hydroxy groups, thus are generally unstable and exhibit surface inactivity. Eased on this founding, the present inventors conducted follow-up tests on the Examples of the above Publications. These tests revealed that the products exhibited almost no water repellancy and remained completely ineffective as long as oil repellancy was concerned.

Furthermore, in accordance with the Examples of the JP Patent Kokoku Nos. 61-48803/1986 and 61-55481/1986, the present inventors conducted similar tracing tests in which previously treated powders were surface-treated and subsequently washed with organic solvents, such as xylene, toluene, chloroform, hexane, methylethylketone, methylisobutylketone and Freon 113. It was revealed that, since the surface coating was mostly removed and was only slightly water-repellant without being oil repellant, the surface coating was simply adhered or partially adsorbed and such that can be easily removed during the pulverizing process. It was also confirmed by the present inventors that, when applied to pressed makeup cosmetics, the powders disclosed in these prior-art publications exhibit unevenness and makeup dry of makeup finish to a marked extent while being devoid of tight adherence feeling.

EXAMPLE 2-1 (Second Aspect) Powder Foundation 350 parts of IPA were charged into 100 parts of sericite having a mean particle size of 5.9 μm and the resulting mass was stirred for 60 minutes, washed with 170 parts of acetone and 350 parts of demineralized water and dried at 50° C. for four days. The thus dried sericite was charged into a solution in 530 parts of methylethylketone in which had been dissolved beforehand: 15 parts of perfluoroalkylsilane (n=7), 1.2 part of aluminum tris (acetyl acetonate), 0.1 part of tetra-n-butylammonium bromide and 5.0 parts of boron trifluoride ethylether complex. The resultant mixture was ball-milled for 17 hours, and methylethylketone was distilled off followed by drying. The resulting dried product was heat-treated (baked) in a curing chamber at 150° C. for 10 hours, mixed into and stirred with 1 lit of methylethylketone, and dried at 50° C. to produce coated powders Ia' exhibiting water and oil repellancy (water and oil repellant sericite). In the case of titanium oxide having a mean particle size of 0.32 μm, water and oil repellant titanium oxide as the coated powders Ib' (produced by the method of the present invention) was obtained by a process similar to that described hereinabove, with the use of 1.3 part of alkyl acetoacetate aluminum diisopropylate as the reactive auxiliary agent.

Powder foundation

The following composition A:

| (A) | water and oil repellant sericite (Ia') | 54 parts |
| --- | --- | --- |
|  | water and oil repellant titanium (Ib') | 10 parts |
|  | talc (mean particle size of 9.0 μm) | 13 parts |
|  | spherical calcium silicate (mean particle size of 4.8 μm) | 4 parts |
|  | red oxide of iron (mean particle size of 0.21 μm) | 4 parts | was mixed is a Henschel mixer for one minute and pulverized in a pulverizer. The pulverized product was transferred to a Henschel mixer, and the following composition B was added thereto:

| (B) | liquid paraffin | 7.8 parts |
| --- | --- | --- |
| | z-etyldodecyl myristate | 5 parts |
| | perfume | 0.2 parts | and the resulting mass was mixed and stirred for 10 minutes, taken out, homogenized in a blower sifter and charged into a container to a powder foundation product.

EXAMPLE 2-2

Powder Eye Shadow 10 parts of titanium oxide (mean particle size: 0.38 μm), 70 parts of white mica (mean particle size: 13.8 μm), 5 parts of red oxide of iron (mean particle size: 0.21 μm) and 15 parts of spherical silica (mean particle size: 5.3 μm) were charged into 300 parts of IPA, stirred for 20 minutes, washed with 200 parts of acetone, washed further with 400 parts of demineralized water thrice and dried at 40° C. for five days.

The thus produced dried powders were charged into a mixture containing 200 parts of Freon 113, 450 parts of 2%-perfluoroalkylsilazane solution in Freon 113 and 8.3 parts of nitrogen trifluoride, mixed, stirred and milled in a ball mill for 24 hours, and Freon was distilled off followed by drying. The thus treated powders were heat-treated (baked) at 130° C. for 24 hours in a curing chamber to produce the coated water and oil repellant powders II'.

Powder eye shadow

The following composition A:

| (A) | coated powders II' | 86 parts |
| --- | --- | --- |
| | titanium coated mica (mean particle size of 5.5 μm) | 5 parts | was mixed in a Henschel mixer for one minute and pulverized in a pulverizer. The pulverized product was then transferred into a Henschel mixer, and thereto added was the following composition B:

| (B) | dimethylpolysiloxane | 4.5 parts |
| --- | --- | --- |
| | liquid paraffin | 4.0 parts |
| | perfume | 0.5 parts | and the resulting mass was mixed and stirred for 8 minutes, taken out, homogenized in a pulverizer and charged into a container resulting in a product.

EXAMPLE 2-3

Foundation

The following composition A:

| (A) | coated powders II' of Example (2 - 2) | 20.0 parts |
| --- | --- | --- |
| | stearic acid | 1.0 parts |
| | cetanol | 2.0 parts |
| | diglycerine triisostearate | 3.0 parts |
| | lanoline | 1.0 parts |

| | squalane | 10.0 parts |
| --- | --- | --- |
| | surfactant | 5.0 parts |
| | butylparaben | 0.1 parts |
| | BHT | 0.1 parts | and the following composition B:

| (B) | glycerine | 6.0 parts |
| --- | --- | --- |
| | thickener | 1.5 parts |
| | demineralized water | 49.3 parts | were dissolved separately and maintained at 80° C. The composition B was added gradually to the composition A and the resulting mixture was stirred thoroughly for emulsification After termination of emulsification, to the mixture was added a composition C:

| (C) | perfume | 1.0 part |
| --- | --- | --- | and the resulting mixture was stirred at 80° C. for 3 minutes, cooled with water to 40° C., taken out and charged into a container resulting in a product.

EXAMPLE 2-4

Pancake 50 parts of sericite (mean particle size, 2.8 μm), 10 parts of spherical magnesium silicate (mean particle size, 5.6 μm), 15 parts of titanium oxide (mean particle size, 0.21 μm), 10 parts of diatomaceous earth (mean particle size, 10.1 μm), 5 parts of red oxide of iron (mean particle size, 0.21 μm) and 4 parts of talc (mean particle size, 1.3 μm) were charged into 350 parts of IPA, stirred for 40 minutes, washed with 250 parts of acetone, washed further with 400 parts of demineralized water and dried at 50° C. for three days. The dried powders were then charged into a solution containing 100 parts of 2%-perfluoroalkylsilazane solution in Freon, 2 parts of perfluoroalkylsilazane (n=4), 200 parts of Freon, 6.5 parts of boron trifluoride ethyl ether complex and 40 parts of titanium isopropoxide, and ball-milled for 15 hours. After Freon was distilled off, the ball-milled product was dried. Thereafter it was heat-treated at 110° C. for five hours in a curing chamber and taken out to produce water and oil repellant powders IV.

The following composition A:

| (A) | coated powders of Example (2 - 1) | 20 parts |
| --- | --- | --- |
| | coated powders of Example (2 - 2) | 23 parts |
| | coated powders of Example (2 - 4) | 40 parts | was charged into a Henschel mixer and thereto added the following composition B:

| (B) | squalane | 5 parts |
| --- | --- | --- |
| | lanoline | 3 parts |
| | dimethylpolysiloxiane | 4 parts | under stirring. After stirring was continued for two minutes, the following composition C:

|     |                   |           |
| --- | ----------------- | --------- |
| (C) | 1, 3 - butylene glycol | 3 parts   |
|     | ethylparaben      | 0.2 parts |
|     | perfume           | 0.5 parts | was added to the mixture, the resulting product was stirred for two minutes, taken out and charged via a blower sifter into a container resulting in a product.

EXAMPLE 2-5

400 parts of IPA were added to 100 parts of sericite (mean particle size, 5.9 μm) and the resulting mass was stirred for 60 minutes, washed with 350 parts of demineralized water and dried at 60° C. for four days. The thus dried sericite was charged into a solution containing 530 parts of toluene, 15 parts of perfluoroalkylsilane (n=7), 1.3 parts of alkyl acetoacetate aluminum diisopropylate and 7.5 parts of boron trifluoride ethyl ether complex, and the resulting product was ball-milled for 20 hours. After toluene was distilled off, the resulting product was dried, heat-treated at 150° C. for 10 hours using a curing chamber, taken out, further admixed and stirred with 1 lit toluene and dried at 50° C. to produce a first baked coating layer exhibiting water and oil repellancy.

On the other hand, after 5 parts of perfluoro alkylsilane (n=3), 5 parts of oleic acid, 5.0 parts of tetra-n-butylammonium bromide and 1.0 part of ethylacetoacetate aluminum diisopropylate had been dissolved in 500 parts of IPA, 100 parts of sericite powders having the above described first baked coating layer on their surfaces were added thereto and ball-milled for 12 hours, taken out and dried after IPA was distilled off. The dried product was then heat-treated at 130° C. for 10 hours, taken out, mixed into 1 lit of IPA, stirred and dried at 50° C. to two-layered coated powders V.

EXAMPLE 2-6

10 parts of titanium oxide, 70 parts of white mica, 5 parts of red oxide of iron and 15 parts of spherical silica, each having the similar mean particle sizes as those shown in Example 2-2, were added to 300 parts of IPA, stirred for 20 minutes, washed with 200 parts of acetone, further washed with 400 parts of demineralized water thrice and dried at 40° C. for five days.

On the other hand, the thus dried and mixed powders were charged into a solution containing 200 parts of Freon 113, 450 parts of 2%-perfluoroalkylsilazane solution in Freon, 8.3 parts of nitrogen trifluoride and 1.5 parts of aluminum tris (acetylacetonate), and the resulting mass was mixed, stirred and milled in a ball mill for 24 hours. After Freon was distilled off, the ball-milled product was dried and heat-treated in a curing chamber at 130° C. for 24 hours resulting in coated powders having a water and oil repellant first baked coating layer on their surfaces.

100 parts of the thus coated powders were charged into a solution containing 530 parts of methylethylketone, 10 parts of perfluoroalkylsilane (n=7), 5 parts of boron trifluoride and 5 parts of isostearic acid, and the resulting mass was ball-milled for 24 hours. After methylethylketone was distilled off, the ball-milled product was dried, heat-treated in a curing chamber at 150° C. for 15 hours, taken out, mixed into and stirred with 1 lit of methylethylketone and dried at 50° C. resulting in two-layered coated powders VI having the second water and oil repellant baked coating layer on the aforementioned first baked coating layer.

In the above Examples (2-1) to (2-6), the material of each of the inorganic base powder sample is assumed to have the following mean particle size after grinding:

sericite (mean particle size, 5.9 μm)→5.3 μm talc (mean particle size, 9.0 μm)→7.9 μm diatomaceous earth (mean particle size, 10.1 μm)→8.9 μm sericite (mean particle size, 2.8 μm)→2.6 μm The mean particle sizes of titanium oxide, red oxide of iron, spherical silica, spherical magnesium silicate and talc (1.3 μm) are thought to remain substantially unchanged after grinding.

Comparative Experiments

The coated powders produced by the method of the inventive second aspect were compared with the conventional cosmetic compositions, based on qualitative evaluation of their water and oil repellant properties.

Samples (a) coated powders Ia' of Ex. 2-1 of the present invention
(b) coated powders Ib' of Ex. 2-1 of the present invention
(c) coated powders II' of Ex. 2-2 of the present invention
(d) coated powders IV of Ex. 2-4 of the present invention
(e) coated powders V of Ex. 2-5 of the present invention
(f) coated powders VI of Ex. 2-6 of the present invention
(g) cosmetic powders surface-treated with a fluorine base resin according to the JP Patent Kokoku No. 61-48803/1986
(h) cosmetic powders treated with a fluorine-containing water and oil repellant agent according to the JP Patent Kokoku No. 61-55481/1986
(i) a mixture of sericite and 1,2,2 trichloro-1,2,2 trifluoroethane

Experimental Procedures

Each 5 g of demineralized water and various oily agents (squalane, oleic acid, isostearyl alcohol and cetyl 2-ethyl hexanoate and Jojoba oil were weighed out into a 20 mlit test tube with plug into which 0.1 g of the samples was introduced and which was shaked 100 times at ambient temperature, allowed to stand for two days, again shaked 100 times and allowed to stand at ambient temperature for two days followed by evaluation.

In preparing the samples (a) to (f), the products obtained in Example 2-1 to 2-6 were taken out and each 20 g of the products was dispersed in 200 g of xylene, stirred for 30 minutes in a magnetic stirrer, taken out, filtered, dried for 24 hours in a dryer maintained at 50° C., taken out and pulverized resulting in samples.

The results of the experiments are shown in Table 2.

TABLE 2

|     | water | squalane | oleic acid | isostearyl alcohol | cetyl 2-ethyl hexanoate | jojoba oil |
| --- | ----- | -------- | ---------- | ------------------ | ----------------------- | ---------- |
| (a) | A     | A        | A          | A                  | A                       | A          |
| (b) | A     | A        | A          | A                  | A                       | A          |
| (c) | A     | A        | A          | A                  | A                       | A          |
| (d) | A     | A        | A          | A                  | A                       | A          |
| (e) | A     | A        | A          | A                  | A                       | A          |
| (f) | A     | A        | A          | A                  | A                       | A          |
| (g) | C     | X        | X          | X                  | X                       | X          |
| (h) | C     | X        | X          | X                  | X                       | X          |

TABLE 2-continued

|   | water | squalane | oleic acid | isostearyl alcohol | cetyl 2-ethyl hexanoate | jojoba oil |
|---|---|---|---|---|---|---|
| (i) | X | X | X | X | X | X |

A, B, C, X: same as in Table 1.

The existence of the strong chemical bond between the coating layer on the powder surface and the inorganic base powders can be ascertained by the experiments as mentioned in the first aspect.

It should be understood that the present invention is not limited to the specific embodiments or disclosure hereinabove mentioned but modification in the art may be done without departing from the gist and scope as disclosed herein and claimed hereinbelow.

What is claimed is:

1. A water and oil repellant coated powder comprising a vapor deposition coating layer of a water and oil repellant agent on the surface of an inorganic base powder, said coating layer being reaction-bonded to active sites on the surface of said inorganic base powder directly without an intermediate layer between said water and oil repellant agent and said surface of said inorganic base powder, wherein said water and oil repellant agent is selected from the group consisting of fluorosilanes, fluorosilazanes and fluorinated hydrocarbons and has fluorine bonded in its main chain.

2. The coated powder according to claim 1 wherein the weight ratio of said inorganic base powder to said water and oil repellant agent is 1:0.005 to 1:0.50.

3. The coated powder according to claim 1 wherein said active site on the surface of the inorganic base powder is sol id acid site, sol id base site or both.

4. The coated powder according to claim 1 wherein said coating layer is a resultant layer of thermal decomposition of the water and oil repellant agent.

5. The coated powder according to claim 2 wherein the weight ratio of said inorganic base powder to said water and oil repellant agent is 1:0.08 to 1:0.45.

6. The coated powder according to claim 5 wherein the weight ratio of said inorganic base powder to said water and oil repellant agent is 1:0.11 to 1:0.40.

7. Makeup cosmetics comprising the water and oil repellant powder of claim 1, 2, 3 or 4.

8. A coated powder for use in cosmetics comprising the product of the process comprising:

reaction bonding a surface activated inorganic base powder with one or both of a water and oil repellant agent selected from the group consisting of fluorosilanes and fluorosilazanes and which has fluorine bonded in its main chain and a nonhydrophilic, water repellant oily agent selected from the group consisting of cosmetically acceptable hydrocarbons, higher fatty acids, oils and fats, higher alcohols and waxes, a reactive auxiliary agent and a primer, and forming a baked coating layer on the surface of said base powder by heat treatment, said baked coating layer being formed of one or both of the water and oil repellant agent and the oily agent and the reactive auxiliary agent.

9. A coated powder for use in cosmetics comprising the product of the process comprising:

reaction bonding a active sites of surface activated inorganic base powder with a first baked coating layer of one or both of a water and oil repellant agent selected from the group consisting of fluorosilanes and fluorosilazanes and which has fluorine bonded in its main chain and a nonhydrophilic, water repellant oily agent selected from the group consisting of cosmetically acceptable hydrocarbons, higher fatty acids, oils and fats, higher alcohols and waxes and a reactive auxiliary agent, and forming a second baked coating layer on the surface of said first baked coating layer by heat treatment, said second baked coating layer being formed of one or both of the water and oil repellant agent and the oily agent and the reactive auxiliary agent to provide a multilayer structure, provided that said second baked coating layer contains the water and oil repellant agent when said first baked coating layer contains no water and oil repellant agent.

10. The coated powder of claim 9, wherein the first baked coating layer comprises the product of the process comprising:

coating an activated inorganic base powder with one or both of a water and oil repellant agent selected from the group consisting of fluorosilanes and fluorosilazanes and which has fluorine bonded in its main chain and a nonhydrophilic, water repellant oily agent selected from the group consisting of cosmetically acceptable hydrocarbons, higher fatty acids, oils and fats, higher alcohols and waxes, a reactive auxiliary agent and a primer, and forming the first baked coating layer by heat treatment.

11. A coated powder for use in cosmetics comprising the product of the process comprising:

reaction bonding a surface activated inorganic base powder with a first baked coating layer of one or both of a water and oil repellant agent selected from the group consisting of fluorosilanes and fluorosilazanes and which has fluorine bonded in its main chain and a nonhydrophilic, water repellant oily agent selected from the group consisting of cosmetically acceptable hydrocarbons, higher fatty acids, oils and fats, higher alcohols and waxes, a reactive auxiliary agent and a primer, and forming a second baked coating layer on the surface of said first baked coating layer by heat treatment, said second baked coating layer being formed of one or both of the water and oil repellant agent and the oily agent and the reactive auxiliary agent to provide a multilayer structure.

12. The coated powder of claim 11, wherein the first baked coating layer on the coated powder comprises the product of the process comprising:

coating an activated inorganic base powder with one or both of a water and oil repellant agent selected from the group consisting of fluorosilanes and fluorosilazanes and which has fluorine bonded in its main chain and a nonhydrophilic, water repellant oily agent selected from the group consisting of cosmetically acceptable hydrocarbons, higher fatty acids, oils and fats, higher alcohols and waxes, a reactive auxiliary agent and a primer, and forming the first baked coating layer by heat treatment.

13. The coated powder of claim 8, 9, 10, 11 or 12, wherein the ratio of inorganic base powder: water and oil repellant agent: primer is 1:(0.004–0.50):(0.001–0.25) by weight.

14. The coated powder of claim 8, 9, 10, 11 or 12, wherein the ratio of inorganic base powder: water and oil repellant agent: primer: reactive auxiliary agent is 1: (0.004–0.50):(0.001–0.25):(0.001–0.3) by weight.

15. A water and oil repellant coated powder comprising the product of the process comprising:

contact-reacting an inorganic base powder with a gaseous water and oil repelling agent selected from the group consisting of fluorosilanes, fluorosilazanes and fluorinated hydrocarbons and which has fluorine bonded in its main chain under heat to form a vapor deposition coating layer of the water and oil repellant agent on the surface of said base powder, said coating layer being bonded to active sites on the surface of said base powder.

16. Makeup cosmetics comprising the coated powder of claim 8, 9, 10, 11 or 12.

17. Makeup cosmetics comprising the coated powder of claim 13.

18. Makeup cosmetics comprising the coated powder of claim 14.

19. The coated powder of claim 1, 8, 9, 10, 11, 12 or 15, wherein the water and oil repellant agent is selected from the group consisting of fluorosilanes and fluorosilazanes of the formulas:

$CF_3(CF_2)_n CH_2—CH_2 Si—R_3$, wherein n=0 to 10;

$(C_n F_{2n+1})_m CH_2—CH_2 Si—R_3$, wherein n=1 to 5, m=1 to 10, $R_3$=H, OH, alkoxy group ($OCH_3$ etc.) or phenyl group ($OC_6H_5$); and (i) $Rf—Si(NH_2)_3$;

(ii) $Rf—Si(NH_2)_2—NH—Si(NH_2)_2$;
    |
    Rf
(dimer of (i))

(iii) 
$$Rf—\underset{\underset{NH_2}{|}}{\overset{\overset{NH_2}{|}}{Si}}—N\overset{H}{|}—\underset{\underset{NH_2}{|}}{\overset{\overset{Rf}{|}}{Si}}—N\overset{H}{|}—\underset{\underset{NH_2}{|}}{\overset{\overset{NH_2}{|}}{Si}}—Rf;$$ and
(trimer of (i));

(iv) oligomers of (i), wherein
$Rf=F\!+\!(CF—CF_2—O)_n$
   $\quad\quad\quad\quad CF_3$ (n = 1 to 10);
or $Rf=C_n F_{2n+1}—$ (n = 1 to 10);
or $Rf=F\!+\!(CF_2—CF_2—O)_{\overline{n}}$ (n = 1 to 10).

20. A water and oil repellant coated powder consisting essentially of a vapor deposition coating layer of a water and oil repellant agent on the surface of an inorganic base powder, said coating layer being reaction-bonded to active sites on the surface of said inorganic base powder, wherein said water and oil repellant agent is selected from the group consisting of fluorosilanes, fluorosilazanes and fluorinated hydrocarbons and has fluorine bonded in its main chain.

\* \* \* \* \*

UNITED STATES PATENT AND TRADEMARK OFFICE
CERTIFICATE OF CORRECTION

PATENT NO.  : 5,458,976
DATED       : October 17, 1995
INVENTOR(S) : Masaakira HORINO and Nami ITO It is certified that error appears in the above-identified patent and that said Letters Patent is hereby corrected as shown below:

On The Title Page, Item [73]:

Assignee:  Pola Chemical Industries, Inc.
           Shizuoka-shi, Shizuoka-ken, JAPAN Signed and Sealed this Eighth Day of October, 1996

Attest:

BRUCE LEHMAN

Attesting Officer    Commissioner of Patents and Trademarks